US006476245B1

United States Patent
Cavell et al.

(10) Patent No.: US 6,476,245 B1
(45) Date of Patent: Nov. 5, 2002

(54) PHOSPHINIMINE METHANIDE TRANSITION METAL CATALYSTS

(75) Inventors: Ronald G. Cavell, Edmonton (CA); Qinyan Wang, Calgary (CA); Ruppa P. Kamalesh Babu, Edmonton (CA); Aparna Kasani, Edmonton (CA)

(73) Assignee: The Governors of the University of Alberta (CA)

( * ) Notice: Subject to any disclaimer, the term of this patent is extended or adjusted under 35 U.S.C. 154(b) by 0 days.

(21) Appl. No.: 09/626,620

(22) Filed: Jul. 26, 2000

(51) Int. Cl.[7] ................................................. C07F 7/08
(52) U.S. Cl. ............................... 556/9; 556/12; 556/19
(58) Field of Search .................................. 556/9, 12, 19

(56) References Cited

U.S. PATENT DOCUMENTS

| | | | | |
|---|---|---|---|---|
| 5,502,128 A | * | 3/1996 | Flores et al. | 526/160 |
| 5,534,474 A | * | 7/1996 | Becker et al. | 502/152 |
| 5,557,023 A | * | 9/1996 | Somogyvari et al. | 585/513 |
| 5,589,555 A | * | 12/1996 | Zboril et al. | 526/64 |
| 5,707,913 A | * | 1/1998 | Schlund et al. | 502/102 |
| 6,060,568 A | * | 5/2000 | Cavell et al. | 526/131 |

FOREIGN PATENT DOCUMENTS

| | | | |
|---|---|---|---|
| EP | 0668295 A1 | * | 8/1995 |
| WO | WO 96/23010 | * | 8/1996 |

OTHER PUBLICATIONS

U.S. application Ser. No. 09/375,943, Cavell et al., filed Aug. 17, 1999.*

U. Zucchini, E. Albizzati and U. Gianni, Synthesis and Properties of Some Titanium and Zirconium Benzyl Derivatives, J. Organometal. Chem., 26 (1971) 357–372.

Von R. Appel and I. Ruppert, Darstellung silylieter Alkylen–bisminophosphorane und ihre Cyclisierung mit Phosphor (V)–fluoriden, Z. anorg. allg. Chem. 406, 131–144 (1974).

Richard A. Andersen, Chloro– and Methyltris[(hexamethyldisilyl) amido]zirconium (IV) and –hafnium (IV), Inorganic Chemistry, vol. 18, No. 6, 1979.

Michael D. Fryzuk, David H. McConville and Steven J. Rettig, Synthesis, structure and hydrogenation of $n^3$–benzyl diphosphine complexes of rhodium and iridium, Journal of Organometallic Chemistry, 445 (1993) 245–256.

Lynda K. Johnson, Christopher M. Killian, and Maurice Brookhart, New Pd(II)– and Ni(II)–Based Catalysts for Polymerization of Ethylene and a–Olefins, J. Am. Chem. Soc. vol. 117, (1995), 6414.

George J.P. Britovsek, Vernon C. Gibson, Brian S. Kimberley, Peter J. Maddox, Stuart J. McTavish, Gregory A. Solan, Andrew J.P. White, and David J. Williams, Novel olefin polymerization catalysts based on iron and cobalt, Chem. Commun., (1998) 849.

* cited by examiner

Primary Examiner—Paul F. Shaver
(74) Attorney, Agent, or Firm—Kenneth H. Johnson

(57) ABSTRACT

The present invention relates to novel complexes of (transition) metals containing ligands having phosphinimine centers bonded to the (transition) metal.

15 Claims, No Drawings

US 6,476,245 B1

PHOSPHINIMINE METHANIDE TRANSITION METAL CATALYSTS

FIELD OF THE INVENTION

The present invention relates to novel catalysts of metals preferably transition metals and to the processes for using such catalysts for olefin polymerization. The catalyst contains at least one phosphinimine center, and a carbon atom or an alkenyl radical bonded to the metal to form a metal heteroatom alkyl bond or a carbene structure, respectively.

BACKGROUND OF THE INVENTION

Currently there is increasing interest in catalysts of transition metals having novel structures.

Recently there has been significant interest in Brookhart's ligand which may complex later transition metals to form a catalyst useful in an olefin polymerization process. Such complexes are disclosed, for example in World Patent Application 96/23010 jointly in the names of the University of Carolina at Chapel Hill and E.I. DuPont published Aug. 1, 1996. The Brookhart et al patent application does not teach the complexes of the present invention.

The recent paper (Chem. Comm (1998) p. 849) by Gibson and coworkers at Imperial College UK (and BP) teach complexes having a novel structure that is dissimilar to the complexes of the present invention. It is postulated that the complexes of Gibson et al. will have utility in the polymerization of certain monomers such as alpha olefins.

There has been a great deal of work recently by both Exxon in the field of metallocene chemistry and by the Dow Chemical Company in single site constrained geometry complexes. As far as applicant has been able to determine none of the chemistry proposed by either Exxon or Dow contain a carbene structure or a constrained alkyl carbon bonded to a transition metal. There are several patents relating to amidinato complexes of transition metals which are suitable for the polymerization of various olefins. U.S. Pat. No. 5,502,128 issued Mar. 26, 1996, assigned to University of Massachusetts, teaches such complexes may be used to polymerize vinyl aromatic monomers; and U.S. Pat. No. 5,707,913 issued Jan. 13, 1998, assigned to BASF, teaches such compounds may be used to polymerize olefins. Neither of these patents disclose complexes of the structure of the present invention.

U.S. Pat. No. 5,557,023 issued September 1996 teaches the use of some complexes of transition metals to oligomerize lower alpha olefins such as ethylene to higher olefins such as hexene and the like. The complexes of the patent do not contain a carbene structure or substituted carbon bonded to the transition metal.

Copending U.S. patent application Ser. No. 09/375,943 filed Aug. 17, 1999 in the name of R. G. Cavell et al. discloses the complexes useful in the catalyst of the present invention.

U.S. Pat. No. 6,060,568 issued May 9, 2000 in the name of the Applicant discloses complexes similar to those of the present invention except that the complexes contain only one $R^7$ and one $R^8$ substituent. The present invention provides for more than one $R^7$ or $R^8$ substituents. The sum of the subscripts a and b is a whole number greater than 2 and up to the sum of the valence and co-ordination number of the metal (i.e. both the electrovalence and coordinate valence).

Applicant has been unable to identify any prior art disclosing the catalyst of the present invention for the polymerization of olefins.

SUMMARY OF THE INVENTION

The present invention provides a process for the polymerization of one or more $C_{2-12}$ alpha olefins in the presence of a complex selected from the group consisting of a complex of formula I:

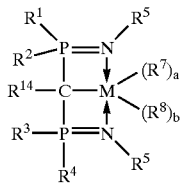

wherein M is a metal atom; $R^1$, $R^2$, $R^3$ and $R^4$ are independently selected from the group consisting of a saturated or unsaturated straight chained, branched or cyclic hydrocarbyl radical which is unsubstituted or substituted by one or more substituents selected from the group consisting of a halogen atom and a $C_{1-6}$, most preferably a $C_{1-4}$ alkyl radical; $R^7$ and $R^8$ are independently selected from the group consisting of a hydrogen atom, a halogen atom, an amide of the formula —$NR^1R^2$, an imide of the formula =$NR^1$, an alkoxide or aryl oxide group of the formula —$OR^1$, a siloxy group of the formula —$OSi(R^1)_3$ wherein $R^1$ and $R^2$ are defined above, and a saturated or unsaturated straight chained, branched or cyclic hydrocarbyl radical which is unsubstituted or substituted by a halogen atom or a $C_{1-6}$ alkyl radical and a Lewis base (neutral coordinating ligands) which may contain a donor heteroatom including but not limited to ethers, tertiary amines, tertiary phosphines and cyclic amines; a and b are integers and a+b is an integer greater than 2 up to the sum of the valence and co-ordination number of M; and each $R^5$ is independently selected from the group consisting of radicals selected from the group consisting of saturated and unsaturated straight chained, branched and cyclic hydrocarbyl radicals, preferably $C_{1-15}$ saturated or unsaturated straight chained, branched or cyclic hydrocarbyl radicals, most preferably $C_{1-8}$ straight or branched alkyl radicals, $C_{6-12}$ cyclic aliphatic or aromatic radicals, radicals of the formula $Si(R^6)_3$ wherein each $R^6$ is independently selected from the group consisting of saturated or unsaturated straight chained, branched or cyclic hydrocarbyl radicals, preferably $C_{1-10}$ saturated or unsaturated straight chained, branched or cyclic hydrocarbyl radicals and radicals of the formula III:

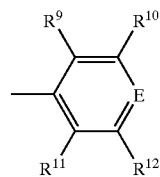

wherein $R^9$, $R^{10}$, $R^{11}$ and $R^{12}$ are independently selected from the group consisting of a hydrogen atom, a fluorine atom, a $NO_2$ radical, a $C_{1-6}$ alkyl radical and a $C_{8-12}$ aryl radical; E is an endocyclic nitrogen atom or a C—CN group; and $R^{14}$ is selected from the group consisting of a hydrogen atom, a sulfur atom, an oxygen atom, an amido radical which is unsubstituted or may be substituted by $C_{1-20}$ alkyl radical, preferably a $C_{1-6}$ alkyl radical or a radical of the formula —$Si(R^6)_3$ wherein $R^6$ is as defined above, a $C_{1-20}$ hydrocarbyl radical, a $C_{6-12}$ aromatic radical and a radical of the formula III as defined above, each of which may contain one or more functional groups including a heteroatom acting as a Lewis base; and optionally $R^{14}$ taken together with the metal may form a ring; and an activator at a temperature from 20 to 250° C. and at a pressure from 15 to 15,000 psi.

The present invention also provides a complex of formula I:

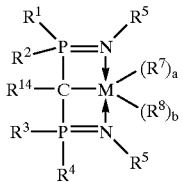

wherein M, $R^1$, $R^2$, $R^3$, $R^4$, $R^5$, $R^7$, $R^8$, $R^{14}$, a and b are as defined above.

DETAILED DESCRIPTION OF THE PREFERRED EMBODIMENTS

The term "scavenger" as used in this specification is meant to include those compounds effective for removing polar impurities from the reaction solvent. Such impurities can be inadvertently introduced with any of the polymerization reaction components, particularly with solvent, monomer and catalyst feed; and can adversely affect catalyst activity and stability. It can result in decreasing or even elimination of catalytic activity, particularly when an activator capable of ionizing the catalyst is also present.

In the catalyst of the present invention, the metal may be any transition metal. It may be an early transition metal such as Y, Ti, Zr, Hf, V or Cr or it may be a later transition metal such as Fe, Co, Ni, Pd or Pt or a post transition metal (Zn) or a lanthanide group, preferably Sm. Preferably the transition metal will be selected from group 3 through 10 (formerly group IIIB through VIII) of the Periodic Table.

In accordance with the present invention $R^1$, $R^2$, $R^3$ and $R^4$ may be independently selected from the group consisting of a saturated or unsaturated straight chained, branched or cyclic hydrocarbyl radical which is unsubstituted or substituted by one or more substituents selected from the group consisting of a halogen atom and a $C_{1-6}$, most preferably a $C_{1-4}$ alkyl radical. Preferably, the hydrocarbyl radicals may be selected from the group consisting of a $C_{1-10}$, preferably $C_{1-8}$, most preferably $C_{1-6}$ straight chained, branched or cyclic alkyl radicals which radicals may be unsubstituted or further substituted, preferably by not more than three substituents selected from the group consisting of $C_{1-4}$ alkyl radicals or a halogen atom, preferably either F or Cl. Additionally, substituents $R^1$, $R^2$, $R^3$ and $R^4$ may be independently selected from the group consisting of $C_{5-14}$ aromatic radicals which radicals are unsubstituted or substituted by up to n−1, wherein n is the number of carbon atoms in the aromatic radical, substituents selected from the group consisting of a halogen atom, preferably F or Cl, a $C_{1-6}$, most preferably a $C_{1-4}$ alkyl radical or an amido radical which is unsubstituted or substituted by up to two $C_{1-6}$, preferably $C_{1-4}$ alkyl radicals.

The substituents $R^1$, $R^2$, $R^3$ and $R^4$ may be selected from the group consisting of a fluorine atom, a chlorine atom, a methyl radical, an ethyl radical, a propyl radical, a butyl radical, a tertiary butyl radical and a phenyl radical.

In some embodiments of the present invention $R^1$ and $R^2$ may be the same. In a further embodiment $R^3$ and $R^4$ may be the same. In a further embodiment of the present invention all of $R^1$, $R^2$, $R^3$ and $R^4$ may be the same.

In the present invention $R^7$ and $R^8$ may be independently selected from the group consisting of a halogen atom preferably a chlorine or fluorine atom, an amide $-NR^1R^2$, an imide of the formula $=NR^1$; an alkoxide or aryl oxide group, $-OR^1$; and an $-OSi(R^1)_3$ group wherein $R_1$ and $R^2$ are defined above; and a saturated or unsaturated straight chained, branched or cyclic hydrocarbyl radical which are unsubstituted or substituted by a halogen atom or a $C_{1-6}$ alkyl radical or a Lewis base (neutral coordinating ligands) which may contain a donor heteroatom including but not limited to ethers preferably $C_{1-6}$ alkyl ethers or $C_{4-8}$ cyclic ethers; tertiary amines preferably $C_{1-6}$ tertiary amines; tertiary phosphines preferably tertiary $C_{1-10}$ phosphines and cyclic amines preferably $C_{4-8}$ cyclic amines (nitrogen containing compounds). The hydrocarbyl radical may be a straight chained or branched $C_{1-10}$ alkyl radical which may be unsubstituted or substituted by a F or Cl atom or up to three $C_{1-6}$, preferably $C_{1-4}$ alkyl radicals. The hydrocarbyl radical may be selected from the group consisting of $C_{5-14}$ aromatic radicals which radicals are unsubstituted or substituted by up to n−1, wherein n is the number of carbon atoms in the aromatic radical, substituents selected from the group consisting of a halogen atom, preferably F or Cl, a $C_{1-6}$, most preferably a $C_{1-4}$ alkyl radical or an amido radical which is unsubstituted or substituted by up to two $C_{1-6}$, preferably $C_{1-4}$ alkyl radicals.

Both a and b are integers and the sum of a+b is an integer greater than 2 and up to the sum of the valence and co-ordination number of M. Typically the sum of a and b may be from 3 to 6 and a and b may be in the range of 2 or 3.

In accordance with the present invention each $R^5$ is independently selected from the group consisting of radicals of a saturated or unsaturated straight chained, branched or cyclic hydrocarbyl radical, preferably $C_{1-15}$ saturated or unsaturated straight chained, branched or cyclic hydrocarbyl radicals, most preferably a $C_{1-8}$ straight or branched alkyl radical and a $C_{6-12}$ cyclic aliphatic or aromatic radical; radicals of the formula $Si(R^6)_3$ wherein each $R^6$ is independently selected from the group consisting of saturated or unsaturated straight chained, branched or cyclic hydrocarbyl radicals, preferably $C_{1-10}$ saturated or unsaturated straight chained, branched or cyclic hydrocarbyl radicals of the formula III:

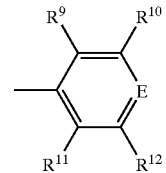

wherein $R^9$, $R^{10}$, $R^{11}$ and $R^{12}$ are independently selected from the group consisting of a hydrogen atom, a fluorine atom, a $NO_2$ radical, a $C_{1-6}$ alkyl radical and a $C_{8-12}$ aryl radical; and E is an endocyclic nitrogen atom or a C—CN group.

Each $R^5$ radical may be selected from the group consisting of radicals of the formula $Si(R^6)_3$ wherein each $R^6$ is independently selected from the group consisting of saturated or unsaturated straight chained, branched or cyclic hydrocarbyl radicals, preferably $C_{1-10}$ saturated or unsaturated straight chained, branched or cyclic hydrocarbyl radicals. Most preferably $R^6$ is selected from $C_{1-8}$, preferably $C_{1-6}$, most preferably $C_{1-4}$ alkyl radicals. Suitable alkyl radicals include methyl, ethyl, propyl and butyl and adamantyl radicals. In a preferred embodiment of this aspect of the invention each $R^6$ radical is the same.

$R^5$ may also be a 4-cyanotetrafluorophenyl radical.

The catalyst of the present invention wherein the $R^7$ and $R^8$ are halogens and may be alkylated, aminated or alkoxylated by reacting with suitable alkylating agents such as LiR or RMgX, aminating agents such as $MNR_2$ or an alkoxylating agent which is an alkali alkoxide (e.g. $M^2OR$ where $M^2$ is selected from the group consisting of alkali metals, preferably lithium). In the alkylating, aminating or alkoxylating agent, the alkyl or alkoxide radical is as defined in $R^7$ and $R^8$ above.

Some hydrocarbon solvents include $C_{5-12}$ hydrocarbons which may be unsubstituted or substituted by $C_{1-4}$ alkyl group, such as pentane, hexane, heptane, octane, cyclohexane, methylcyclohexane and hydrogenated naphtha. An additional solvent is Isopar E ($C_{8-10}$ aliphatic solvent, Exxon Chemical Co.). The solvent may be aromatic such as benzene, toluene or xylene. The solvent may also be a simple or branched ether in which the alkyl radicals may contain from 1 to 10 carbon atoms or a polyether thereof such as diethyl ether and diglyme. The product is recovered using conventional procedures illustrated in the examples. The reaction may be carried out from room temperature (20° C.) to about 150° C.

In the compounds of formula I, M, $R^1$, $R^2$, $R^3$, $R^4$, $R^5$, $R^7$, $R^8$, a and b are as defined above and $R^{14}$ is selected from the group consisting of a hydrogen atom, a sulfur atom, an oxygen atom, an amido radical unsubstituted or may be substituted by a $C_{1-20}$ alkyl radical preferably a $C_{1-6}$ alkyl radical or a radical of the formula —$Si(R^6)_3$ wherein $R^6$ is as defined above, a $C_{1-20}$ hydrocarbyl radical, a $C_{6-12}$ aromatic radical and a radical of the formula III as defined above, each of which may contain one or more functional groups including a heteroatom acting as a Lewis base such as:

(i) an amido group which may be unsubstituted or substituted by up to two substituents selected from the group consisting of a $C_{1-20}$ alkyl radical preferably a $C_{1-6}$ alkyl radical; a radical of the formula —$Si(R^6)_3$ wherein $R^6$ is as defined above; a phosphine group which may be unsubstituted or further substituted by a substituent selected from the group consisting of a hydrogen atom, a halogen atom preferably fluorine or chlorine, a $C_{1-6}$ alkyl or alkoxide radical, and an amide radical which is unsubstituted or substituted by up to two $C_{1-6}$ alkyl radicals;

(ii) an imido group which is unsubstituted or may be substituted by $C_{1-20}$ alkyl or $C_{6-12}$ aromatic radical, preferably a $C_{1-6}$ alkyl radical; a radical of the formula —$Si(R^6)_3$ wherein $R^6$ is as defined above; an amido as defined above; a phosphine group which may be unsubstituted or substituted by a substituent selected from the group consisting of a halogen atom preferably fluorine or chlorine, a $C_{1-6}$ alkyl or alkoxide radical, and an amide radical which is unsubstituted or substituted by up to two $C_{1-6}$ alkyl radicals;

(iii) a phosphine group which may be unsubstituted or substituted by a substituent selected from the group consisting of a hydrogen atom, a halogen atom preferably fluorine or chlorine, a $C_{1-6}$ alkyl or alkoxide radical, and an amide radical which is unsubstituted or substituted by up to two $C_{1-6}$ alkyl radicals; and (iv) a carbonyl or carboxyl group.

When $R^{14}$ is a sulfur atom, an oxygen atom, an amido radical unsubstituted or may be substituted by $C_{1-20}$ alkyl radical $R^{14}$ together with M will form a ring.

$R^{14}$ may be a straight, branched alkyl group which may or may not form a ring with M.

However, if $R^{14}$ contains one or more functional groups as defined above, it may also form a ring with the metal and the functional groups may be exocyclic (pendant to the ring) or endocyclic (forming part of the ring).

In some cases where $R^{14}$ is short or the heteroatom on $R^{14}$ is close to the carbon behind the metal, the ring may be constrained.

The compounds of the formula I, as defined above, may be prepared by the reaction of a compound of formula II:

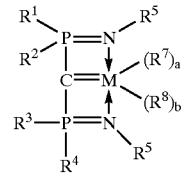

wherein $R^1$, $R^2$, $R^3$, $R^4$, $R^5$, $R^7$, $R^8$, a, b and M are as defined above with (i) molecules of the type AB wherein A is selected from the group consisting of a hydrogen atom, a $C_{1-20}$ alkyl group, a $C_{6-12}$ aryl group, an amino group (as substituted as defined in $R^{14}$), a $C_{1-20}$ alkoxy group, a $C_{1-20}$ alkylthio group, a $C_{6-12}$ aryloxy group, a $C_{6-12}$ arylthio group, and a radical of the formula III as defined above; and B is selected from the group consisting of a hydrogen atom provided that A is not a hydrocarbyl radical or a hydrogen atom and halogen atom;

(ii) compounds of the formula F=C=G wherein F and G are independently selected from the group consisting of an O or S atom preferably O; and radicals of the formula =N—$R^{15}$, wherein $R^{15}$ is a $C_{1-20}$ hydrocarbyl radical, a $C_{6-12}$ aromatic radical, and a radical of the formula —$Si(R^6)_3$ wherein $R^6$ is as defined above; =P—$(R^{16})_d$ wherein d is 1 or 3; and $R^{16}$ is selected from the group consisting of a hydrogen atom, a halogen atom, a $C_{1-20}$ hydrocarbyl radical, a $C_{1-20}$ alkoxide radical, a $C_{6-12}$ aromatic radical, a $C_{6-12}$ aryloxide radical, and radicals of the formula —$Si(R^6)_3$ or —O—$Si(R^6)_3$ wherein $R^6$ is as defined above.

The preparation of compounds of formula 11 is disclosed in U.S. Pat. No. 6,060,568 issued May 9, 2000 assigned to The Governors of the University of Alberta (the text of which is incorporated herein by reference).

The reaction of the compounds of formula II with a molecule of the type AB, a compound of the formula F=C=G may be carried out in a hydrocarbyl solvent which may be aliphatic or aromatic (such as toluene or benzene or similar solvents) at temperatures from room temperature (e.g. 20° C.) up to about 120° C. for a period of time from a few minutes (e.g. about 5 minutes) to several days, typically from 1 to 12 hours. The compound of formula I may be recovered by crystallization.

Compounds which contain an unsaturation include for example $CO_2$, O=C=N-adamantyl, O=C=N(p-tolyl) and O=C=NCy where Cy is cyclohexyl.

The catalyst of the present invention wherein $R^7$ and $R^8$ are not alkyl may be alkylated (either partially or fully). Some alkylating agents are Grignard agents of the formula RMgX and organolithium reagents of the formula LiR wherein R is a $C_{1-10}$ alkyl radical and X is a halogen and alkyl aluminum reagents. Alkyl aluminum reagents include trialkyl aluminum and alkyl aluminum halides (i.e. $(R)_xAlX_{3-x}$ wherein R is a $C_{1-10}$ alkyl radical, X is a halogen, x is 1 or 2 and MAO as described below).

The polymerization may be conducted at temperatures from about 20 to about 250° C. Depending on the product being made, this temperature may be relatively low such as from 20 to about 120° C. (preferably less than 120° C., i.e. 119° C. and below). The pressure of the reaction may be as high as about 15,000 psig for the older high pressure processes or may range from about 15 to 4,500 psig. The temperatures for solution processes tend to be higher, typically from 120 to 250° C.

Solution polymerization processes are fairly well known in the art. These processes are conducted in the presence of an inert hydrocarbon solvent typically a $C_{5-12}$ hydrocarbon which may be unsubstituted or substituted by $C_{1-4}$ alkyl group such as pentane, hexane, heptane, octane, cyclohexane, methylcyclohexane or hydrogenated naphtha. An additional solvent is Isopar E ($C_{8-12}$ aliphatic solvent, Exxon Chemical Co.).

Suitable olefin monomers may be ethylene and $C_{3-20}$ mono- and diolefins. Preferred monomers include ethylene and $C_{3-12}$ alpha olefins which are unsubstituted or substituted by up to two $C_{1-6}$ alkyl radicals. Illustrative non-limiting examples of such alpha olefins are one or more of propylene, 1-butene, 1-pentene, 1-hexene, 1-octene and 1-decene.

The polyethylene polymers which may be prepared in accordance with the present invention typically comprise not less than 60, preferably not less than 70, most preferably not less than 80 weight % of ethylene and the balance of one or more $C_{4-10}$ alpha olefins, preferably selected from the group consisting of 1-butene, 1-hexene and 1-octene.

The complexes of the present invention may require the use of a support. An exemplary list of support materials include metal oxides (such as silica, alumina, silica-alumina, titania and zirconia), metal chlorides (such as magnesium chloride), talc, polymers (including polyolefins), ion exchangeable layer materials (or compounds), partially pre-polymerized mixtures of a group 4 metal complex, activators and polymers, spray dried mixtures of the group 4 metal complex, and activators and fine "inert" particles (as disclosed, for example, in European Patent Application 668,295 (to Union Carbide)).

The preferred support material is silica. In a particularly preferred embodiment, the silica has been treated with an alumoxane (especially methylalumoxane or "MAO") prior to the deposition of the group 4 metal complex. The procedure for preparing "supported MAO" which is described in U.S. Pat. No. 5,534,474 (to Witco) is preferred for reasons of economy. It will be recognized by those skilled in the art that silica may be characterized by such parameters as particle size, pore volume and residual silanol concentration. The pore size and silanol concentration may be altered by heat treatment or calcining. The residual silanol groups provide a potential reaction site between the alumoxane and the silica (and, indeed, some off gassing is observed when alumoxane is reacted with silica having residual silanol groups). This reaction may help to "anchor" the alumoxane to the silica (which, in turn, may help to reduce reactor fouling).

The preferred particle size, preferred pore volume and preferred residual silanol concentration may be influenced by reactor conditions. Typical silicas are dry powders having a particle size of from 1 to 200 microns (with an average particle size of from 30 to 100 being especially suitable); pore size of from 50 to 500 Angstroms; and pore volumes of from 0.5 to 5.0 cubic centimeters per gram. As a general guideline, the use of commercially available silicas, such as those sold by W. R. Grace under the trademarks Davison 948 or Davison 955, are suitable.

The activator may be selected from the group consisting of:

(i) an aluminoxane; and (ii) an activator capable of ionizing the catalyst (which may be used in combination with an alkylating activator).

The aluminoxane activator may be of the formula $(R^{20})_2AlO(R^{20}AlO)_mAl(R^{20})_2$ wherein each $R^{20}$ is independently selected from the group consisting of $C_{1-20}$ hydrocarbyl radicals, m is from 0 to 50, and preferably $R^{20}$ is a $C_{1-4}$ alkyl radical and m is from 5 to 30. The aluminoxane activator may be used prior to the reaction but preferably in situ alkylation is typical (e.g. alkyl groups replacing leaving ligands, hydrogen or halide groups).

Activation with aluminoxane generally requires a molar ratio of aluminum in the activator to the catalyst from 20:1 to 1000:1. MAO may be the higher end of the above noted range.

The activator of the present invention may be a combination of an alkylating activator which also serves as a scavenger other than aluminoxane in combination with an activator capable of ionizing the catalyst.

The alkylating activator (which may also serve as a scavenger) may be selected from the group consisting of: $(R)_pMgX_{2-p}$ wherein X is a halide, each R is independently selected from the group consisting of $C_{1-10}$ alkyl radicals, preferably $C_{1-8}$ alkyl radicals and p is 1 or 2; RLi wherein R is as defined above; $(R)_qZnX_{2-q}$ wherein R is as defined above, X is halogen and q is 1 or 2; $(R)_sAlX_{3-s}$ wherein R is as defined above, X is halogen and s is an integer from 1 to 3. Preferably, in the above compounds R is a $C_{1-4}$ alkyl radical and X is chlorine. Commercially available compounds include triethyl aluminum (TEAL), diethyl aluminum chloride (DEAC), dibutyl magnesium ($(Bu)_2Mg$) and butyl ethyl magnesium (BuEtMg or BuMgEt).

The activator capable of ionizing the catalyst may be selected from the group consisting of:

(i) compounds of the formula $[R^{15}]^+[B(R^{18})_4]^-$ wherein B is a boron atom, $R^{15}$ is a cyclic $C_{5-7}$ aromatic cation or a triphenyl methyl cation and each $R^{18}$ is independently selected from the group consisting of phenyl radicals which are unsubstituted or substituted with from 3 to 5 substituents selected from the group consisting of a fluorine atom, a $C_{1-4}$ alkyl or alkoxy radical which is unsubstituted or substituted by a fluorine atom, and a silyl radical of the formula —Si—$(R^{19})_3$ wherein each $R^{19}$ is independently selected from the group consisting of a hydrogen atom and a $C_{1-4}$ alkyl radical; and (ii) compounds of the formula $[(R^{16})_tZH]^+[B(R^{18})_4]^-$ wherein B is a boron atom; H is a hydrogen atom; Z is a nitrogen atom or phosphorus atom; t is 2 or 3; and $R^{16}$ is selected from the group consisting of $C_{1-8}$ alkyl radicals, a phenyl radical which is unsubstituted or substituted by up to three $C_{1-4}$ alkyl radicals, or one $R^{16}$ taken together with the nitrogen atom to form an anilinium radical and $R^{18}$ is as defined above; and (iii) compounds (activators) of the formula $B(R^{18})_3$ wherein $R^{18}$ is as defined above.

In the above compounds, preferably $R^{18}$ is a pentafluorophenyl radical, $R^5$ is a triphenylmethyl cation, Z is a nitrogen atom and $R^{16}$ is a $C_{1-4}$ alkyl radical or $R^{16}$ taken together with the nitrogen atom to form an anilinium radical which is substituted by two $C_{1-4}$ alkyl radicals.

The activator capable of ionizing the catalyst abstracts one or more of $R^7$ or $R^8$ so as to ionize the catalyst center into a cation, but not to covalently bond with the catalyst;

and to provide sufficient distance between the ionized catalyst and the ionizing activator to permit a polymerizable olefin to enter the resulting active site.

Examples of compounds capable of ionizing the catalyst include the following compounds:

triethylammonium tetra(phenyl)boron,
tripropylammonium tetra(phenyl)boron,
tri(n-butyl)ammonium tetra(phenyl)boron,
trimethylammonium tetra(p-tolyl)boron,
trimethylammonium tetra(o-tolyl)boron,
tributylammonium tetra(pentafluorophenyl)boron,
tributylammonium tetra(pentafluorophenyl)boron,
tri(n-butyl)ammonium tetra(o-tolyl)boron,
N,N-dimethylanilinium tetra(phenyl)boron,
N, N-diethylanilinium tetra(phenyl)boron,
N,N-diethylanilinium tri(phenyl)n-butylboron,
N,N-2,4,6-pentamethylanilinium tetra(phenyl)boron,
di-(isopropyl)ammonium tetra(pentafluorophenyl)boron,
dicyclohexylammonium tetra(phenyl)boron,
triphenylphosphonium tetra(phenyl)boron,
tri(methylphenyl)phosphonium tetra(phenyl)boron,
tri(dimethylphenyl)phosphonium tetra(phenyl)boron,
tropillium tetrakispentafluorophenyl borate,
triphenylmethylium tetrakispentafluorophenyl borate,
benzene (diazonium) tetrakispentafluorophenyl borate,
tropillium phenyltrispentafluorophenyl borate,
triphenylmethylium phenyltrispentafluorophenyl borate,
benzene (diazonium) phenyltrispentafluorophenyl borate,
tropillium tetrakis (2,3,5,6-tetrafluorophenyl) borate,
triphenylmethylium tetrakis (2,3,5,6-tetrafluorophenyl) borate,
benzene (diazonium) tetrakis (3,4,5-trifluorophenyl) borate,
tropillium tetrakis (3,4,5-trifluorophenyl) borate,
benzene (diazonium) tetrakis (3,4,5-trifluorophenyl) borate,
tropillinum tetrakis (1,2,2-trifluoroethenyl) borate,
triphenylmethylium tetrakis (1,2,2-trifluoroethenyl) borate,
benzene (diazonium) tetrakis (1,2,2-trifluoroethenyl) borate,
tropillium tetrakis (2,3,4,5-tetrafluorophenyl) borate,
triphenylmethylium tetrakis (2,3,4,5-tetrafluorophenyl) borate, and
benzene (diazonium) tetrakis (2,3,4,5-tetrafluorophenyl) borate.

Readily commercially available activators which are capable of ionizing the catalyst include:
N,N-dimethylaniliniumtetrakispentafluorophenyl borate, triphenylmethylium tetrakispentafluorophenyl borate, and trispentafluorophenyl boron.

If the catalyst is activated with a combination of an aluminum alkyl compound (generally other than aluminoxane), and a compound capable of ionizing the catalyst; the molar ratios of catalyst:metal in the alkylating agent (e.g. Al):metalloid (e.g. boron or phosphorus) in the activator capable of ionizing the catalyst (e.g. boron) may range from 1:1:1 to 1:100:5. Preferably, the alkylating activator is premixed/reacted with the catalyst and the resulting alkylated species is then reacted with the activator capable of ionizing the catalyst.

In a solution polymerization, the monomers are dissolved/dispersed in the solvent either prior to being fed to the reactor or for gaseous monomers, the monomer may be fed to the reactor so that it will dissolve in the reaction mixture. Prior to mixing, the solvent and monomers are generally purified to remove polar moieties. The polar moieties or catalyst poisons include water, oxygen, metal impurities, etc. Preferably steps are taken before provision of such into the reaction vessel, for example by chemical treatment or careful separation techniques after or during the synthesis or preparation of the various components. The feedstock purification prior to introduction into the reaction solvent follows standard practices in the art (e.g. molecular sieves, alumina beds and oxygen removal catalysts) are used for the purification of ethylene, alpha olefin and optional diene. The solvent itself as well (e.g. cyclohexane and toluene) is similarly treated. In some instances, out of an abundance of caution, excess scavenging activators may be used in the polymerization process.

The feedstock may be heated prior to feeding into the reactor. However, in many instances it is desired to remove heat from the reactor so the feedstock may be at ambient temperature to help cool the reactor.

Generally, the components may be premixed in the solvent for the reaction or fed as separate streams to the reactor. In some instances, premixing is desirable to provide a reaction time for the catalyst components prior to entering the reaction. Such an "in line mixing" technique is described in a number of patents in the name of DuPont Canada Inc. For example, it is described in U.S. Pat. No. 5,589,555 issued Dec. 31, 1996.

The reactor may comprise a tube or serpentine reactor used in the "high pressure" polymerizations or it may comprise one or more reactors or autoclaves. It is well known that the use in series of two such reactors each of which may be operated so as to achieve different polymer molecular weight characteristics. The residence time in the reactor system will depend on the design and the capacity of the reactor. Generally, the reactors should be operated under conditions to achieve a thorough mixing of the reactants. On leaving the reactor system, the solvent is removed and the resulting polymer is finished in a conventional manner.

The present invention will be illustrated by the following non-limiting examples in which, unless otherwise specified, part means parts by weight (e.g. grams) and per cent means weight per cent.

Synthesis of Ligands and Metal Carbene Complexes
General Experimental Conditions for Catalyst Synthesis All experimental manipulations were performed under rigorously anaerobic conditions using Schlenk techniques or an argon-filled glovebox with an efficient recirculator. Solvents were dried and distilled under argon prior to use. Hexane and toluene were distilled from Na-K and Na respectively. NMR solvents benzene-$d_6$ and toluene-$d_8$ were freshly vacuum transferred from Na-K. Commercial (Aldrich) supplies of bis(diphenylphosphino)methane (dppm), $Me_3SiN_3$, $ZrCl_4$ and $HfCl_4$ were used as obtained. NMR spectra were recorded using Bruker® WH-200, 300 and 400 spectrometers with reference to the deuterium signal of the solvent employed. The $^1H$ NMR chemical shifts are reported in ppm from external $Me_4Si$ and the 31P NMR spectra are reported in ppm from external 85% $H_3PO_4$. Positive values reflect shifts downfield. Infrared spectra were recorded on a Nicolet® 7199 infrared spectrometer.

Preparation of Ligands
Preparation of $CH_2[Cy_2P=NSiMe_3]_2$

To a solution of dcpm, $\{Cy_2P\}_2CH_2$, {literature preparation: Fryzuk, M. D.; McConville, D. H.; Rettig, S. J.; J. Organomet. Chem. 1993, 445, 245–256.} (3.97 g, 9.72 mmol) in 60 mL of toluene was added trimethylsilyl azide (6 mL, 45.79 mmol) with stirring. The solution was heated to reflux at 110° C. for 48 hours. Solvent was evaporated under vacuum to obtain microcrystalline solid which was washed twice with hexane and dried (Yield: 4.85 g, 85.6%).

IR (Nujol mull): 2666 w, 2653 w, 1449 s, 1376 m, 1348 m, 1302 s, 1264 s, 1244 s, 1233 s, 1209 m, 1173 m, 1154 m, 1119 w, 1078 w, 1045 w, 1028 w, 1004 m, 913 w, 896 m, 852 s, 827 s, 787 s, 776 s, 751 s, 675 m, 663 m, 633 m, 571 w, 526 m. $^1$H NMR (C$_6$D$_6$): δ1.95 (b. t, 4 H, CH—Cy methine), 1.7 (m, CH$_2$—Cy methylene), 1.62 (d, $^2J_{PH}$=12.2 Hz, 2 H, PCH$_2$P methylene), 1.40–1.05 (m, CH$_2$—Cy methylene), 0.38 (s, 18 H, CH$_3$Si methyl). $^{13}${$^1$H} NMR (C$_6$D$_6$): δ39.5 (m, 4 C, CH—Cy, methine), 27.1 (s, 4 C, para Cy), 27.0 (s, 8 C, ortho Cy), 26.8 (s, 4 C, meta Cy), 26.5 (s, 4 C, meta Cy), 21.6 (t, $^1J_{PC}$=61.6 Hz, 1 C, P CH$_2$P methylene), 5.3 (s, 6 C, CH$_3$Si). $^{13}$C{$^1$H,$^{31}$p} (C$_6$D$_6$): δ39.5 (s, 4 CH—Cy, methine), 27.1 (s, 4 C, para Cy), 27.0 (s, 8 C, ortho Cy), 26.8 (s, 4 C, meta Cy), 26.5 (s, 4 C, meta Cy), 21.6 (s, 1 C, P CH$_2$P methylene), 5.3 (s, 6 C, CH$_3$Si). $^{31}$P{$^1$H} NMR (C$_6$D$_6$): δ14.6 (2 P). Analysis calculated for C$_{31}$H$_{64}$N$_2$P$_2$Si$_2$: C, 63.87; H, 11.06; N, 4.81. Found: C, 63.55; H, 11.22; N, 4.63.

Preparation of CH$_2$[Ph$_2$P=NSiMe$_3$]$_2$

As described in the literature {Appel, R.: Ruppert, I. Z.: Anorg. Allg. Chem. 1974, 406, 131–144.}.

Preparation of CH$_2$(Ph$_2$P=NAd)$_2$

Adamantyl azide (1.66 g, 9.37 mmol) was added to a solution of bis(diphenylphosphino)methane (dppm) (1.80 g, 4.68 mmol) in 60 mL of toluene. The mixture was heated to reflux at 110° C. for 2 days. The solution was then cooled to room temperature, concentrated to about 20 mL and maintained at −15° C. to yield, after about 12 hours, a microcrystalline solid which was filtered and dried (Yield: 2.56 g, 80%). $^1$H NMR (toluene-d$_8$): δ7.87 (b. s, 8 H, ortho-Ph), 7.05 (b. s, 12 H, meta and para-Ph), 3.48 (b. t, 2 H, CH$_2$), 1.99 (b.s, 3 H, CH—Ad), 1.93 (b. s, 6 H, CH$_2$—Ad), 1.59 (b. s, 6 H, CH$_2$—Ad). $^{31}$P{$^1$H} NMR (toluene-d$_8$): δ−15.4 (s).

Analysis calculated for C$_{45}$H$_{52}$N$_2$P$_2$: C, 79.15; H, 7.68; N, 4.10. Found: C, 78.58; H, 7.93; N, 4.03.

Preparation of Me$_3$Si=NPPh$_2$CH$_2$Ph$_2$P=NC$_6$F$_4$-p-CN

To a solution of bis(diphenylphosphoranotrimethylsilylimino)methane (11.17 g, 20 mmol) in dichloromethane a solution of pentafluorobenzonitrile (4.05 g, 21 mmol) in dichloromethane (35 mL) was added at room temperature. Immediately the solution turned yellow and after stirring for 12 hours became orange. The solvent was completely removed in vacuo leaving the slightly orange colored crude product which was recrystallized from acetonitrile giving the pure ligand (yield 10.28, g, 78%; white cubic crystals; mp 198–200° C.). Analysis calculated for C$_{35}$H$_{31}$F$_4$N$_3$P$_2$Si: C, 63.77; H, 4.69; N, 6.36. Found: C, 63.01; H, 4.70; N, 6.46. MS (EI, m/z): 659 (M$^+$). $^1$H NMR (CD$_2$Cl$_2$): phenyl rings δ7.80 to 7.74 ppm, 7.57 to 7.29 ppm (m, 20H); PCH$_2$ P methylene, δ3.75 ppm ('t', 2H, $^2J_{HP}$ 13.39 Hz); Me$_3$ Si methyl δ−0.29 ppm (s, 9H). $^{19}$F{$^1$H} NMR (CDCl$_3$): ortho δ−140.17 ppm (m, 2F); meta δ153.32 ppm (m, 2F). $^{29}$Si{$^1$H} NMR (CDCl$_3$), δ−10.59 ppm (d, $^2J_{SiP}$ 20.49 Hz).

Preparation of {Li$_2$C{Ph$_2$P=NSiMe$_3$}$_2$}

Colorless crystalline bis (diphenylphosphoranotrimethysilylimino)methane H$_2$C{Ph$_2$P=NSiMe$_3$}$_2$ (1.0 g, 1.79 mmol) was dissolved in 20 mL of toluene. To this toluene solution, PhLi (0.30 g, 3.59 mmol) was added with stirring. The reaction mixture was stirred at room temperature for 3 days. Approximately 100 mg of colorless solid was removed by filtration. The clear solution was reduced to one-half volume and allowed to stand at room temperature for 48 hours whereupon colorless crystals deposited. (Yield: 0.62 g, 60.7%). IR (Nujol mull): 1434 m, 1244 s, 1190 s, 1174 m, 1101 s, 1067 s, 852 s, 832 s, 764 m, 747 m, 725 m, 709 m, 696 s, 675 w, 663 w, 646 s, 618 w, 606 w, 539 s, 512 m. $^1$H NMR (C$_6$D$_6$): δ7.53–7.49 (m, phenyl), 7.04–6.93 (m, phenyl), 0.04 (s, CH$_3$Si methyl). $^{13}$C{$^1$H} NMR (C$_6$D$_6$): δ139.0 (m, 4 C, ipso phenyl), 131.0 (t, $^2J_{PC}$=4.5 Hz, 8 C, ortho phenyl), 129.0 (s, 4 C, para phenyl), 127.8 (s, 8 C, meta phenyl), 4.4 (s, 6C, CH$_3$Si). $^{31}$P {$^1$H} NMR (C$_6$D$_6$): δ13.7 (2 P). Analysis calculated for C$_{31}$H$_{38}$Li$_2$N$_2$P$_2$Si$_2$: C, 65.25; H, 6.71; N, 4.91. Found: C, 65.27; H, 6.69; N, 4.60.

Preparation of Metal Carbene and Related Derivatives

Preparation of [ZrCl$_2${C(Cy$_2$=NSiMe$_3$)$_2$}] (Zr-3C)

[ZrCl$_2${N(SiMe$_3$)$_2$}$_2$] (0.5 g, 1.04 mmol) {literature preparation: Andersen, R. A.; Inorg. Chem. 1979, 18, 1724–1725} was dissolved in 15 mL of toluene by stirring. Solid bisimine ligand, CH$_2$(Cy$_2$P=NSiMe$_3$)$_2$ (0.604 g, 1.04 mmol) was added to the solution which was then heated to reflux at 130° C. for five days. The pale yellow solution was concentrated to about 10 mL and left at room temperature for 24 hours whereupon pale yellow crystals formed which were isolated by filtration (0.42 g). The mother liquor was concentrated to 5 mL, hexane was added and the total mixture was cooled to −15° C. for 24 hours which yielded a second crop of product (0.15 g). Yield: 0.57 g, 75.2%). IR (Nujol mull): 1447 s, 1403 w, 1377 m, 1356 w, 1321 s, 1258 s, 1246 s, 1200 w, 1192 m, 1176 m, 1167 w, 1111 m, 1049 b.s, 998 m, 915 w, 887 m, 837 s, 779 m, 769 s, 753 m, 746 s, 679 m, 651 s, 634 m, 609 s, 551 s, 509 w, 495 m, 484 w, 465 w. $^1$H NMR (C$_6$D$_6$): δ2.1–1.1 (b. m, 40 H, CH$_2$—Cy methylene), 1.76 (m, 4 H, CH—Cy methine) (as assigned from a $^1$H-$^{13}$C HMQC expt.), 0.51 (s, 18 H, CH$_3$Si methyl). $^{13}$C {$^1$H} NMR (C$_6$D$_6$): δ86.9 (t, $^1J_{PC}$=156.0 Hz, 1 C, PCP carbene), 40.3 (m,, 4 C, CH—Cy, methine), 26.8 (m, 8 C, ortho Cy), 26.6 (s, 4 C, para Cy), 26.3 (s, 4 C, meta Cy), 26.1 (s, 4 C, meta Cy), 3.4 (s, 6 C, CH$_3$Si). $^{13}$C {$^1$H, $^{13}$P} NMR (C$_6$D$_6$): δ86.9 (s, 1 C, PCP carbene), 40.3 (s, 4 C, CH—Cy, methine), 26.9 (s, 4 C, ortho Cy), 26.8 (s, 4 C, ortho Cy), 26.6 (s, 4 C, para Cy), 26.3 (s, 4 C, meta Cy), 26.1 (s, 4 C, meta Cy), 3.4 (s, 6 C, CH$_3$Si). $^{31}$P{$^1$H} NMR (C$_6$D$_6$): δ35.5 (2 P). Analysis calculated for C$_{31}$H$_{62}$Cl$_2$N$_2$P$_2$Si$_2$Zr: C, 50.11; H, 8.41; N, 3.77. Found: C, 49.97; H, 8.68; 3.63.

Preparation of [ZrMe$_2${C(Cy$_2$=NSiMe$_3$)$_2$}]Zr-3C(Me$_2$)

To a toluene solution (~20 mL) of Zr-3C (0.207 g, 0.278 mmol) at −78° C. was added a 3M diethyl ether solution of MeMgBr (0.241 mL, 0.723 mmol). The reaction mixture was warmed to room temperature, stirred for 2 hours and pumped to dryness. The solid was extracted with heptane (3×15 mL) and the heptane extract was slowly evaporated to dryness. Colorless crystals of Zr-3C(Me$_2$) were obtained (136 mg, plus ~30 mg left in flask).

Preparation of [ZrCl$_2${C(Ph$_2$P=NSiMe$_3$)$_2$}] (Zr-3D)

[ZrCl$_2${N(SiMe$_3$)$_2$}$_2$] {literature preparation: Andersen, R. A.; Inorg. Chem. 1979, 18, 1724–1725.} (1.0 g, 2.07 mmol) was dissolved in 20 mL of toluene by stirring. The bisimine ligand, CH$_2$(Ph$_2$P=NSiMe$_3$)$_2$, (1.16 g, 2.08 mmol) was added as a solid to the solution which was then heated to reflux at 130° C. for 24 hours. The resultant pale yellow solution was concentrated to nearly 5 mL and mixed with 5 mL of hexane. Upon cooling overnight, a pale yellow crystalline solid was obtained which was isolated by filtration (Yield: 1.05 g, 70.5%). IR (Nujol mull): 1653 w, 1480 w, 1462 m, 1436 s, 1378 w, 1304 s, 1251 s, 1179 w, 1156 w, 1112 s, 1061 s, 1042 m, 1026 m, 999 w, 842 s, 785 m, 771 w, 753 w, 747 w, 737 w, 714 s, 695 s, 652 s, 631 m, 613 s, 571 m, 522 s. $^1$H NMR (C$_6$D$_6$): δ7.6 (m, phenyl), 6.98 (m, phenyl), 6.92 (m, phenyl), 6.90 (m, phenyl), 0.25 (s, 18 H, CH$_3$Si methyl). $^{13}$C {$^1$H} NMR (C$_6$D$_6$): δ134.2 (m, 4 C, ipso phenyl), 131.5 (t, $^2J_{PC}$=6.0 Hz, 8 C, ortho phenyl), 131.2 (s, 4 C, para phenyl), 128.5 (t, $^3J_{PC}$=6.2 Hz, 8 C, meta phenyl), 101.7 (t, $^1J_{PC}$=146 Hz, 1 C, PCP carbene), 2.6 (s, 6 C, CH$_3$Si). $^{13}$C{$^1$H, $^{31}$P} NMR (C$_6$D$_6$): δ134.2 (s, 4 C, ipso phenyl), 131.5 (s, 8 C, ortho phenyl), 131.2 (s, 4 C, para phenyl), 128.5 (s, 8 C, meta phenyl), 101.7 (s, 1 C, PCP carbene), 2.6 (s, 6 C, CH$_3$Si). $^{31}$P{$^1$H} NMR (C$_6$D$_6$): δ15.7 (2 P). Analysis calculated for C$_{31}$H$_{38}$Cl$_2$N$_2$P$_2$Si$_2$Zr: C, 51.79; H, 5.33; N, 3.90. Found: C, 51.41; H, 5.78; N, 3.80.
Preparation of [ZrCl$_2${C(Ph$_2$P=NSiMe$_3$)$_2$}] (Zr-3D) Method B To a suspension of ZrCl$_4$(THF)$_2$ (0.13 g, 0.35 mmol) in diethyl ether (5 mL) the dilithium salt Li$_2$C(Ph$_2$P=NSiMe$_3$)$_2$ (0.20 g, 0.35 mmol) was added with stirring at room temperature. The mixture was stirred at room temperature for 2 days. Diethyl ether was removed and the resultant solid product was extracted with 5 mL of toluene and filtered to remove LiCl. The toluene solution was then concentrated to half the initial volume and the solution cooled to −15° C. for 2 days whereupon colorless crystals of {ZrCl$_2${C(Ph$_2$P=NSiMe$_3$)$_2$} precipitated (Yield: 0.16 g, 63.5%). All spectroscopic and analytical data indicated that the product was identical with the compound identified as {ZrCl$_2${C(Ph$_2$P=NSiMe$_3$)$_2$} as described above.

Preparation of HfCl$_2${C(Cy$_2$P=NSiMe$_3$)$_2$

The complex, [HfCl$_2${N(SiMe$_3$)$_2$}$_2$] (0.2 g, 0.35 mmol) was dissolved in 10 mL of toluene. Solid CH$_2$(Cy$_2$P=NSiMe$_3$)$_2$ (0.204 g, 0.35 mmol) was added to this solution with stirring and the colorless solution was heated at 140° C. for seven days. The resultant pale yellow solution was concentrated and cooled to −15° C. for 24 hours to obtain colorless crystals which were isolated by filtration (Yield: 0.21 g, 72.1%). IR (Nujol mull): 1447 s, 1404 w, 1377 w, 1356 w, 1320 s, 1297 w, 1260 s, 1246 s, 1202 w, 1192 w, 1176 w, 1168 w, 1112 m, 1024 b.s, 915 w, 887 m, 836 b.s, 783 m, 771 s, 754 s, 747 s, 707 w, 679 m, 654 s, 635 m, 615 s, 552 s, 542 m, 495 m, 485 m, 464 w. $^1$H NMR (400.1 MHz, C$_6$D$_6$, 298 K): δ2.1–1.1 (b.m, 40 H, methylene-Cy and 4 H, methine-Cy), 0.47 (s, 18 H, methyl-TMS). $^{13}$C {$^1$H} NMR (100.6 MHz, C$_6$D$_6$, 298 K): δ66.6 (t, $^1J_{PC}$=158.0 Hz, 1 C, quaternary C-PCP), 40.7 (m, 4 C, methine-Cy), 26.8 (m, 8 C, ortho methylene-Cy), 26.6 (s, 4 C, para methylene-Cy), 26.4 (s, 4 C, meta methylene-Cy), 26.3 (s, 4 C, meta methylene-Cy), 3.5 (s, 6 C, methyl-TMS). $^{31}$P{$^1$H} NMR (161.9 MHz, C$_6$D$_6$, 298 K): δ32.6 (2 P). Analysis calculated for C$_{31}$H$_{62}$Cl$_2$HfN$_2$P$_2$Si$_2$: C, 44.84; H, 7.53; N, 3.37. Found: C, 45.04; H, 7.98; N, 3.29.
Preparation of HfCl$_2${C(Ph$_2$P=NSiMe$_3$)$_2$ In a similar fashion, [HfCl$_2${N(SiMe$_3$)$_2$}$_2$] (0.104 g, 0.18 mmol) in toluene solution was treated with solid CH$_2$(Ph$_2$P=NSiMe$_3$)$_2$ (0.102 g, 0.18 mmol) and heated at 140° C. for 3 days. The solution was reduced to a small volume and layered with hexane. After 2 days at ambient temperature, colorless crystals were deposited which were isolated by filtration (Yield: 0.11 g, 74.8%). IR (Nujol mull): 1589 w, 1574 w, 1480 w, 1463 m, 1436 s, 1378 m, 1311 s, 1251 s, 1181 w, 1156 m, 1111 s, 1070 m, 1057 s, 1037 s, 999 m, 843 s, 787 s, 772 m, 754 m, 738 m, 716 s, 696 s, 654 s, 631 m, 622 s, 615 m, 576 m, 524 s. $^1$H NMR (400.1 MHz, C$_6$D$_6$, 298 K): δ7.63 (m, phenyl), 6.97 (m, phenyl), 6.91 (m, phenyl), 0.22 (s, 18 H, CH$_3$Si methyl). $^{13}$C {$^1$H} NMR (100.6 MHz, C$_6$D$_6$, 298 K): δ134.7 (m, 4 C, ipso phenyl), 131.5 (t, $^2J_{PC}$=6.0 Hz, δ8 C, ortho phenyl), 131.0 (s, 4 C, para phenyl), 128.5 (t, $^3J_{PC}$=5.6 Hz, δ8 C, meta phenyl), 84.6 (t, $^1J_{PC}$=145.0 Hz, 1 C, quaternary C-PCP), 2.6 (s, 6 C, methyl-TMS). $^{31}$P{$^1$H} NMR (161.9 MHz, C$_6$D$_6$, 298 K): δ12.2 (2 P). Analysis calculated for HfCl$_2${C(Ph$_2$P=NSiMe$_3$)$_2$}] 0.5 toluene, C$_{34.5}$H$_{42}$Cl$_2$HfN$_2$P$_2$Si$_2$: C, 48.62; ; H, 4.97; N, 3.29. Found: C, 148.24; H, 5.21; N, 3.34.
Preparation of [Zr{C(Ph$_2$P=NSiMe$_3$)$_2$}(CH$_2$C$_6$H$_5$)$_2$] (Zr-6D)

[Zr(CH$_2$C$_6$H$_5$)$_4$] (1.0 g, 2.19 mmol) {literature preparation: Zucchini, U.; Albizzati, E.; Giannini, U.; J. Organomet. Chem. 1971, 26, 357–372.} was added to 15 mL of toluene and stirred at room temperature. To the pale yellow brown suspension was added solid bisimine ligand, CH$_2$(Ph$_2$P=NSiMe$_3$)$_2$ (1.226 g, 2.19 mmol) at room temperature. The reaction mixture was stirred at room temperature for 2 days during which time a pale brown microcrystalline solid precipitated. The product was isolated by filtration, washed with a few mL of hexane and dried (Yield: 1.34 g, 73.5%). IR (Nujol mull): 1900–1650 w, 1591 m, 1488 m, 1481 m, 1466 m, 1436 m, 1378 m, 1334 w, 1283 s, 1260 s, 1249 s, 1216 m, 1204 m, 1173 m, 1151 w, 1110 s, 1016 b.s, 971 m, 880 w, 834 b.s, 793 w, 776 s, 764 m, 743 s, 734 m, 720 s, 693 s, 656 s, 620 m, 614 m, 562 s. $^1$H NMR (C$_6$D$_6$): δ7.34 (m, phenyl), 7.26 (m, phenyl), 7.24 (m, phenyl), 7.02 (m, phenyl), 6.93 (m, phenyl), 2.62 (s, 4H, CH$_2$Ph methylene), 0.09 (s, 18 H, CH$_3$Si methyl). $^{13}$C {$^1$H} (C$_6$D$_6$): δ147.7 (s, 2 C, ipso benzyl), 135.9 (m, 4 C, ipso phenyl), 131.6 (t, $^2J_{PC}$=6.0 Hz, 8 C, ortho phenyl), 130.5 (s, 4 C, ortho benzyl), 128.9 (s, 4 C, meta benzyl), 128.2 (t, $^3J_{PC}$=6.5 Hz, 8 C, meta phenyl), 126.8 (s, 4 C, para phenyl), 121.2 (s, 2 C, para benzyl), 84.7 (t, $^1J_{PC}$=164 Hz, 1 C, PCP carbene), 68.8 (s, 2 C, CH$_2$Ph methylene), 3.6 (s, 6 C, CH$_3$Si). $^{13}$C {$^1$H, $^{31}$P} NMR (C$_6$D$_6$): δ147.7 (s, 2 C, ipso benzyl), 135.9 (s, 4 C, ipso phenyl), 131.6 (s, 8 C, ortho phenyl), 130.5 (s, 4 C, ortho benzyl), 128.9 (s, 4 C, meta benzyl), 128.2 (s, 8 C, meta phenyl), 126.8 (s, 4 C, para phenyl), 121.2 (s, 2 C, para benzyl), 84.7 (s, 1 C, PCP carbene), 68.8 (s, 2 C, CH$_2$Ph methylene), 3.6 (s, 6 C, CH$_3$Si). $^{31}$P{$^1$H} NMR (C$_6$D$_6$): δ−12.4 (2 P). Analysis calculated for C$_{45}$H$_{52}$N$_2$P$_2$Si$_2$Zr: C, 65.10; H, 6.31; N, 3.37. Found: C, 65.65; H, 6.03; N, 3.31.
Preparation of [{(Me$_3$SiN=PCy$_2$)$_2$CH}Li(OEt$_2$)]

Colorless crystalline bis(dicyclohexylphosphoranotrimethylsilylimino)methane H$_2$C{Cy$_2$P=NSiMe$_3$}$_2$ (0.2 g, 0.34 mmol) was dissolved in 5 mL of toluene. To this solution MeLi was added (1.4 M solution in diethyl ether, 0.49 mL, 0.69 mmol) with stirring. The reaction mixture was stirred at room temperature for 3 days. Concentration of the mother solution to nearly half the original volume and leaving the flask at −15° C. for 48 hours yielded colorless crystals. (Yield: 0.145 g, 63.8%). IR (Nujol mull): 1269 m, 1242 30 s, 1223 s, 1211 s, 1197 s, 1167 s, 1151 s, 1113 m, 1071 w, 1007 m, 987 s, 893 m, 875 m, 850 s, 822 s, 777 m, 752 s, 730 w, 666 m, 641 w, 601 m, 562 s. $^1$H NMR (C$_6$D$_6$): δ3.39 (q, CH$_2$, Et$_2$O), 2.05–1.24 (m, cyclohexyl), 1.09 (t, CH$_3$, Et$_2$O), 0.03 (s, CH$_3$Si), −0.02 (s, CH, P—CH—P). $^{13}$C {$^1$H} NMR (C$_6$D$_6$): δ65.2 (s, CH$_2$, Et$_2$O), 41.2 (d, $^1J_{PC}$=63.0 Hz, ipso cyclohexyl), 27.5 (m, ortho & para cyclohexyl), 27.0 (s, meta cyclohexyl), 15.1 (s, CH$_3$, Et$_2$O), 5.3 (t, $^1J_{PC}$=128.6 Hz, CH, P—CH—P) 5.08 (s, CH$_3$Si). $^{31}$P{$^1$H} NMR (C$_6$D$_6$): δ36.7 (2 P). Analysis calculated for C$_{35}$H$_{73}$LiN$_2$OP$_2$Si$_2$: C, 63.43; H, 11.10; N, 4.23. Found: C, 63.19; H, 10.97 N, 4.30.
Preparation of [ZrCl$_2${HC(Ph$_2$P=NSiMe$_3$)$_2$}(OAd)]

The zirconium dichloride carbene complex, [ZrCl$_2${C(Ph$_2$P=NSiMe$_3$)$_2$}] (0.120 g, 0.17 mmol) was dissolved in 5 mL of toluene. To this colorless solution was added solid adamantanol (0.025 g, 0.17 mmol). With stirring a pale yellow solution was obtained. After 30 minutes, the solution was concentrated to nearly half of the original volume and mixed with few mL of hexane. Upon cooling overnight, a micro-crystalline solid was deposited which was isolated by filtration (Yield: 0.096 g, 66.0%). $^1$H NMR (toluene-d$_8$, 25° C.): δ7.95 (b, phenyl), 7.09 (b, phenyl), 6.83 (b, phenyl), 6.63 (b, phenyl), 2.28 (t, $^2J_{PH}$=2.7 Hz, 1 H, methine P—C—P), 2.17 (b.s, 6H, methylene Ad), 2.02 (b.s, 3H, methine Ad), 1.53 (b.dd, 6H, methylene Ad), 0.53 (s, 18H, methyl CH$_3$Si). $^{31}$P NMR (toluene-d$_8$, 25° C.): δ20.1 (b.s, 2P).

Preparation of [ZrCl$_2${C(O)(NAd))C(Ph$_2$P=NSiMe$_3$)$_2$}] (KB-103)

Solid adamantyl isocyanate (AdNCO) (0.049 g, 0.28 mmol) was added to a stirred, colorless solution of [ZrCl$_2${C (Ph$_2$P=NSiMe$_3$)$_2$}] (0.2 g, 0.28 mmol) in 10 mL of toluene. A white precipitate formed immediately. The resultant suspension was heated at 120° C. for few minutes to dissolve the precipitate. On cooling to room temperature, colorless crystals of the product precipitated which were separated by filtration (Yield: 0.185 g, 74.2%). $^1$H NMR (C$_6$D$_6$): δ8.23 (b.q, phenyl), 7.42 (b.q, phenyl), 7.12 (m, phenyl (toluene)), 7.06 (m, phenyl (toluene)), 7.01 (m, phenyl (toluene)), 6.64 (b.t, phenyl), 6.52 (b.t, phenyl), 2.12 (b.s, 6H, CH$_2$—Ad methylene), 2.10 (s, CH$_3$ toluene), 1.88 (b.s, 3H, CH—Ad methine), 1.62 (b.d, $^2J_{HH}$=12.0 Hz, 3H, CH$_2$—Ad methylene), 1.42 (d, $^2J_{HH}$=12.0 Hz, 3H, CH$_2$—Ad methylene), 0.55 (s, 18 H, CH$_3$Si methyl). $^{13}$C {$^1$H} NMR (C$_6$D$_6$): δ159.8 (t, 1C, $^2J_{PC}$=6.9 Hz, quaternary C=O), 137.9 (s, 2C, ipso phenyl (toluene)), 134.3 (t, $^2J_{PC}$=5.5 Hz, 8 C, ortho phenyl), 132.7 (s, 4 C, para phenyl), 131.98 (t, $^3J_{PC}$=5.4 Hz, 8 C, meta phenyl), 131.6 (s, 4 C, ortho phenyl (toluene)), 130.1 (m, 4C, ipso phenyl), 129.3 (s, 4C, meta phenyl (toluene)), 125.6 (s, 2 C, para phenyl (toluene)), 57.6 (s, 1C, Ad quaternary carbon), 39.5 (s, 3C, CH$_2$—Ad methylene), 36.9 (s, 3C, CH$_2$—Ad methylene), 30.1 (s, 3C, CH—Ad methine), 24.7 (t, $^1J_{PC}$=98.0 Hz, 1 C, quaternary PCP carbon), 21.4 (s, CH$_3$ (toluene)), 4.6 (s, 6 C, CH$_3$Si). $^{31}$P{$^1$H} NMR (C$_6$D$_6$): δ24.6 (2 P).

Preparation of [HfCl$_2${C(O)(NAd))C(Ph$_2$P=NSiMe$_3$)$_2$}]

Solid adamantyl isocyanate (0.044 g, 0.25 mmol) was added to a stirred colorless solution of [HfCl$_2${C (Ph$_2$P=NSiMe$_3$)$_2$}] (0.2 g, 0.25 mmol) in 10 mL of toluene. The reaction mixture was stirred at room temperature for an hour and left to stand at room temperature for two days. During that period colorless crystals formed which were subsequently isolated by filtration (0.17 g). The remaining mother liquor was concentrated to about 4 mL, layered with hexane and left to stand at −15° C. In two days second fraction of colorless crystals were obtained which were separated by filtration (0.064 g). The total yield was 0.234 g, 0.20 mmol, 80.8%. IR (Nujol mull): 1634 s, 1590 w, 1457 s, 1438 s, 1377 m, 1308 w, 1266 m, 1255 s, 1234 s, 1186 w, 1115 s, 1054 s, 1008 s, 924 w, 841 s, 773 s, 749 s, 727 s, 711 s, 695 m, 675 w, 659 m, 647 w, 616 m, 529 s. $^1$H NMR (C$_6$D$_6$): δ8.24 (b.q, phenyl), 7.43 (b.q, phenyl), 7.08 (m, phenyl (toluene)), 7.04 (m, phenyl (toluene)), 7.01 (m, phenyl (toluene)), 6.65 (b.t, phenyl), 6.52 (b.t, phenyl), 2.12 (b.s, 6H, CH$_2$—Ad methylene), 2.10 (s, 6H, CH$_3$ toluene), 1.90 (b.s, 3H, CH—Ad methine), 1.62 (b.d, $^2J_{HH}$=11.7 Hz, 3H, CH$_2$—Ad methylene), 1.43 (b.d, $^2J_{HH}$=11.7 Hz, 3H, CH$_2$—Ad methylene), 0.54 (s, 18 H, CH$_3$Si methyl). $^{13}$C {$^1$H} NMR (C$_6$D$_6$): δ159.7 (t, 1C, $^2J_{PC}$=6.4 Hz, quaternary C=O), 137.8 (s, 2C, ipso phenyl (toluene)), 134.3 (t, $^2J_{PC}$=5.5 Hz, 8 C, ortho phenyl), 132.6 (s, 4 C, para phenyl), 131.9 (t, $^3J_{PC}$=5.2 Hz, 8 C, meta phenyl), 131.6 (s, 4 C, ortho phenyl (toluene)), 130.3 (m, 4C, ipso phenyl), 129.3 (s, 4C, meta phenyl (toluene)), 125.6 (s, 2 C, para phenyl (toluene)), 56.6 (s, 1C, Ad quaternary carbon), 39.6 (s, 3C, CH$_2$—Ad methylene), 36.9 (s, 3C, CH$_2$—Ad methylene), 30.2 (s, 3C, CH—Ad methine), 25.2 (t, $^1J_{PC}$=97.1 Hz, 1 C, quaternary PCP carbon), 21.4 (s, 2 C, CH$_3$ (toluene)), 4.7 (s, 6 C, CH$_3$Si). $^{31}$P{$^1$H} NMR (C$_6$D$_6$): δ24.8 (2 P). Analysis calculated for C$_{45.5}$H$_{57}$Cl$_2$HfN$_3$OP$_2$Si$_2$: C, 53.08; H, 5.58; N, 4.08. Found: C, 53.58; H, 5.73; N, 3.94. (The crystal became opaque when it was taken out of solvent and slowly loses the lattice solvent molecules. The analysis was calculated for the formula [HfCl$_2${C(O)(NAd))C(Ph$_2$P=NSiMe$_3$)$_2$}].0.5C$_6$H$_5$CH$_3$).

Preparation of HfNp$_2${C(Ph$_2$P=NSiMe$_3$)$_2$}

Solid neo-pentyl lithium (0.037 g, 0.47 mmol) was added to a stirred toluene solution (10 mL) containing [HfCl$_2${C (Ph$_2$P=NSiMe$_3$)$_2$}].0.5 toluene (0.2 g, 0.24 mmol) at room temperature. After 24 hours the suspension was filtered and evaporated to dryness. The residual solid was dissolved in few mL of hexane. This solution was cooled at −15° C. for 2 days. Colorless crystals obtained were collected by filtration. Yield: 0.12 g, 56%. $^1$H NMR (400.1 MHz, C$_6$D$_6$, 298 K): δ7.67 (m, 8 H, o-Ph), 6.97 (m, 12 H, m-Ph and p-Ph), 1.41 (s, 18 H, CH$_3$—Np), 1.19 (s, 4 H, CH$_2$—Np), 0.22 (s, 18 H, CH$_3$—SiMe$_3$). $^{13}$C {$^{1H}$} NMR (100.6 MHz, C$_6$D$_6$, 298 K): δ137.2 (m, ipso-Ph), 131.8 (t, $^2J_{PC}$=5 Hz, o-Ph), 130.4 (s, p-Ph), 127.9 (t, $^3J_{PC}$=6 Hz, m-Ph), 98.5 (s, CH$_2$—Np), 71.6 (t, $^1J_{PC}$=160 Hz, quaternary C—PCP), 36.7 (s, CH$_3$—Np), 36.5 (s, quaternary C—Np), 4.2 (s, CH$_3$—SiMe$_3$). $^{31}$P{$^1$H} NMR (161.9 MHz, C$_6$D$_6$, 298 K): δ10.3 (s). Analysis calculated for C$_{41}$H$_{60}$HfN$_2$P$_2$Si$_2$: C, 56.12; H, 6.89; N, 3.19. Found: C, 55.72; H, 6.80; N, 3.12.

Preparation of Hf(AdCN)Cl$_2${C(Ph$_2$P=NSiMe$_3$)$_2$}

Solid adamantyl nitrile (0.038 g, 0.24 mmol) was added to a stirred toluene solution (10 mL) of [HfCl$_2${C (Ph$_2$P=NSiMe$_3$)$_2$}].0.5 toluene (0.2 g, 0.24 mmol) at room temperature. After one hour, the solution was concentrated to one-third of the original volume and left standing at room temperature for three days. Colorless crystals deposited which were collected by filtration. Yield: 0.18 g, 81%. IR (Nujol mull): 2276 m, 2252 w (vCN). $^1$H NMR (400.1 MHz, C$_6$D$_6$, 298 K): δ7.69 (m, 8 H, o-Ph), 7.00 (m, 12 H, m-Ph and p-Ph), 1.62 (b.s, 6 H, CH$_2$—Ad), 1.48 (b.s, 3 H, CH—Ad), 1.24 (b.d, 6 H, CH$_2$—Ad), 0.26 (s, 18 H, CH$_3$—SiMe$_3$). $^{13}$C {$^1$H} NMR (100.6 MHz, C$_6$D$_6$, 298 K): δ135.5 (m, ipso-Ph), 131.6 (t, $^2J_{PC}$=5 Hz, o-Ph), 130.9 (s, p-Ph), 128.3 (t, $^3J_{PC}$=6 Hz, m-Ph), 125.4 (s, quaternary C—CN), 83.4 (t, $^1J_{PC}$=153 Hz, quaternary C—PCP), 39.4 (s, CH$_2$—Ad), 35.5 (s, CH$_2$—Ad), 30.2 (s, quaternary C—Ad), 27.1 (s, CH—Ad), 2.8 (s, CH$_3$—SiMe$_3$). $^{31}$P{$^1$H} NMR (161.9 MHz, C$_6$D$_6$, 298 K): δ11.4 (s). Analysis calculated for C$_{42}$H$_{53}$Cl$_2$HfN$_3$P$_2$Si$_2$: C, 52.15; H, 5.52; N, 4.34. Found: C, 52.23; H, 5.12; N, 4.25.

Preparation of HfCl$_2$HN(p-tolyl)){HC(Ph$_2$P=NSiMe$_3$)$_2$}

Solid toluidine (0.019 g, 0.18 mmol) was added to a stirred toluene solution (10 mL) of [HfCl$_2${C (Ph$_2$P=NSiMe$_3$)$_2$}].0.5 toluene (0.15 g, 0.18 mmol) at room temperature. A white solid precipitated within one hour which was collected and dissolved in THF (5 mL). The resultant clear pale yellow solution was cooled at −15° C. for 3 days whereupon crystals deposited which were collected by filtration. The room temperature NMR spectrum of the product in THF-d$_8$ displayed broad peaks. However, at low temperature (−40° C.) sharp signals were observed which were assignable to two geometrical isomers of the product complex. Yield: 0.11 g, 71%. IR (Nujol mull): 3330 w (vNH). $^1$H NMR (400.1 MHz, C$_6$D$_6$, 313 K): δ7.94 (b.s, 8 H, o-Ph), 7.32 (b.s, 4 H, p-Ph), 7.07 (b.s, δ8 H, m-Ph), 6.82 (b.s, Ph-tolyl), 6.46 (b.s, NH-tolyl), 2.36 (b.s, CH—PCP), 2.22 (b.s, CH$_3$-tolyl), 0.24 (b.s, 18 H, CH$_3$—SiMe$_3$). $^{31}$P{$^1$H} NMR (161.9 MHz, C$_6$D$_6$, 313 K): δ22.2 (b.s). Analysis calculated for C$_{38}$H$_{47}$Cl$_2$HfN$_3$P$_2$Si$_2$: C, 49.97; H, 5.19; N, 4.60. Found: C, 49.76; H, 5.32; N, 4.50.

Preparation of $ZrCl_2\{(C(NCy)NCy)C(Ph_2P=NSiMe_3)_2\}$

Solid dicyclohexylcarbodiimide (0.057 g, 0.28 mmol) was added to a stirred solution of $[ZrCl_2\{C(Ph_2P=NSiMe_3)_2\}]$ (0.20 g, 0.28 mmol) in 10 mL of toluene at room temperature. The white solid which precipitated immediately was isolated by filtration and redissolved in 10 mL of THF. This solution was layered with few mL of toluene for crystallization. After 2 days at −15° C., colorless crystals were deposited which were again isolated by filtration. Yield: 0.27 g, 0.24 mmol, 86%. IR (Nujol mull): 1595 s (vCN), $^1$H NMR (400.1 MHz, $C_6D_6$, 298 K): δ7.80 (m, 4 H, o-Ph) 7.46 (m, 8 H, m-Ph), 7.32 (m, 4 H, o-Ph), 7.20 (m, 4 H, p-Ph), 7.13–7.06 (m, 5 H, Ph-toluene), 3.92 (b.tt, 1 H, ipso-Cy), 3.65 (m, THF), 3.16 (b.tt, 1 H, ipso-Cy), 2.50 (b.dd, 2 H, p-Cy), 2.31 (s, 3 H, $CH_3$-toluene), 2.18 (b.d, 2 H, o-Cy), 1.88 (b.d, 2 H, o-Cy), 1.70 (m, 2 H, o-Cy), 1.38 (m, 8 H, m-Cy), 0.91 (m, 2 H, o-Cy), 0.45 (b.dd, 2 H, p-Cy), 0.01 (s, 18 H, $CH_3$—$SiMe_3$). $^{13}$C $\{^1H\}$ NMR (100.6 MHz, $C_6D_6$, 298 K): δ148.7 (b.t, $^2J_{PC}$=4 Hz, quaternary C—CNCy), 138.4 (s, 1C, ipso-toluene), 133.9 (m, o-Ph), 133.0 (m, ipso-Ph), 133.1 (s, p-Ph), 129.6 (s, o-toluene), 129.1 (t, $^3J_{PC}$=6 Hz, m-Ph), 128.9 (s, m-toluene), 128.8 (t, $^3J_{PC}$=6 Hz, m-Ph), 127.5 (m, ipso-Ph), 126.0 (s, p-toluene), 59.5 (s, ipso-Cy), 57.5 (s, ipso-Cy), 34.8 (s, o-Cy), 30.9 (s, o-Cy), 27.4 (s, m-Cy), 27.3 (s, p-Cy), 27.2 (s, p-Cy), 25.8 (s, m-Cy), 21.6 (s, $CH_3$-toluene), 15.5 (t, $^1J_{PC}$=96.0 Hz, quaternary C—PCP), 4.1 (s, $CH_3$—$SiMe_3$). $^{31}$P$\{^1H\}$ NMR (161.9 MHz, $C_6D_6$, 298 K): δ21.0 (s). Analysis calculated for $C_{51}H_{58}Cl_2N_4P_2Si_2Zr$: C, 60.21; H, 6.74; N, 5.51. Found: C, 59.95; H, 7.07; N, 5.66.

Polymerization Conditions and Results

In the examples, the pressures given are gauge pressures. The following abbreviations and terms are used:

Branching: reported as the number of methyl groups per 1000 methylene groups in the polymer. It is determined by FT-IR.

Polydispersity: weight average molecular weight (Mw) divided by number average molecular weight (Mn).

DSC: differential scanning calorimetry.

GPC: gel permeation chromatography.

MeOH: methanol.

PMAO-IP: a type of polymethylaluminoxane.

Anhydrous toluene was purchased from Aldrich and purified over molecular sieves prior to use. PMAO-IP was purchased from Akzo-Nobel and contained 13.5 weight % of Al. $B(C_6F_5)_3$ was purchased from Boulder Scientific Inc. and used without further purification. $[CPh_3][B(C_6F_5)_4]$ was purchased from Asahi Glass Inc.; lot #: 980224.

Polymer molecular weights and molecular weight distributions were measured by GPC (Waters 150-C) at 140° C. in 1,2,4-trichlorobenzene calibrated using polyethylene standards.

FT-IR was conducted on a Nicolet Model 750 Magna IR spectrometer.

DSC was conducted on a DSC 220 C from Seiko Instruments. The heating rate is 10° C./minute from 0 to 200° C.

Part A: Solution Phase Polymerization

All the solution polymerization experiments described below were conducted using an Autoclave Engineers Zipperclave reactor (500 mL). All the chemicals (solvent, catalyst and cocatalyst) were fed into the reactor batchwise except ethylene which was fed on demand. No product was removed during the polymerization reaction. As are known to those skilled in the art, all the feed streams were purified prior to feeding into the reactor by contact with various absorption media to remove catalysts killing impurities such as water, oxygen, sulfur and polar materials. All components were stored and manipulated under an atmosphere of purified argon or nitrogen. The reactor uses a programmable logical control (PLC) system with Wonderware 5.1 software for the process control. Ethylene polymerizations were performed in the reactor equipped with an air driven stirrer and an automatic temperature control system.

The catalyst was dissolved in toluene. Polymerization temperature is as indicated in the table below. The polymerization reaction time is typically 10 minutes. The reaction was terminated by adding 5 mL of methanol to the reactor and the polymer was recovered by evaporation of the solvent. The polymerization activities were calculated based on the ethylene consumption.

Examples 1–14 were conducted on a solution semi-batch reactor (SBR).

SBR Experimental Conditions with MAO Activation

| | |
|---|---|
| Cyclohexane | 216 mL |
| Catalyst Concentration | 200 μmol/L |
| PMAO-IP | Al/Zr = 300 (mol/mol) |
| Reaction Temperature | 160° C. |
| Reactor Pressure | 140 psig total |
| Stirring Speed | 2000 rpm |

SBR Experimental Conditions with Tritylborate Activation

| | |
|---|---|
| Cyclohexane | 216 mL |
| Catalyst Concentration | 200 μmol/L |
| PMAO-IP | 1 mmol/L as impurity scavenger |
| $[CPh_3][B(C_6F_5)_4]$ | 210 μmol/L |
| Reaction Temperature | 160° C. |
| Reactor Pressure | 140 psig total |
| Stirring Speed | 2000 rpm |

| Examples (1–18) | Catalyst Code | Cocatalyst | Activity gPE/mmol cat * hr | Mw * 10$^{-3}$ | Mn * 10$^{-3}$ | PD |
|---|---|---|---|---|---|---|
| 1[a] | Zr-3D | PMAO-IP | 14.2 | 52.5 | 0.45 | 116.7 |
| 2[a] | Zr-3C | PMAO-IP | 22.7 | 67.3 | 0.25 | 269.2 |
| 3[b] | Zr-3C | $[CPh_3][B(C_6F_5)_4]$ | 70.6 | 643.6 | 139.1 | 4.63 |

-continued

| Examples (1–18) | Catalyst Code | Cocatalyst | Activity gPE/ mmol cat * hr | Polymer Properties | | |
|---|---|---|---|---|---|---|
| | | | | Mw * 10$^{-3}$ | Mn * 10$^{-3}$ | PD |
| 4$^c$ | Zr-6D | [CPh$_3$][B(C$_6$F$_5$)$_4$] | 11.6 | 153.9 | 38.1 | 4.04 |
| 5$^d$ | Zr-6D | [CPh$_3$][B(C$_6$F$_5$)$_4$] | 42.7 | 535.1 | 78.7 | 6.8 |
| 6$^c$ | Zr-6D | B(C$_6$F$_5$)$_3$ | 9.12 | 316.2 | 20.1 | 15.73 |
| 7$^e$ | Zr-6D | [CPh$_3$][B(C$_6$F$_5$)$_4$] | 14.4 | 199.2 | 3.45 | 57.7 |
| 8$^c$ | Zr-3C-Me2 | [CPh$_3$][B(C$_6$F$_5$)$_4$] | 56.8 | 449.1 | 127.1 | 3.53 |
| 9$^f$ | Zr-6D | [CPh$_3$][B(C$_6$F$_5$)$_4$] | 10.5 | 94.8 | 2.08 | 45.6 |
| 10$^f$ | Zr-3C-Me2 | [CPh$_3$][B(C$_6$F$_5$)$_4$] | 8.22 | | | |
| 11$^b$ | KB-103 | [CPh$_3$][B(C$_6$F$_5$)$_4$] | 498.7 | | | |
| 12$^a$ | KB-103 | PMAO-IP | 129.0 | | | |
| 13$^g$ | DuPont Catalyst | PMAO-IP | 49.46 | 15 | 1.1 | 14.4 |
| 14$^a$ | Cp$_2$ZrCl$_2$ | PMAO-IP | 1339.9 | 7.8 | 2.2 | 4.6 |

$^a$SBR standard MAO screening conditions.
$^b$In-situ alkylation: PMAO-IP (Al/M = 20) premixed with catalyst, the mixture and tritylborate solution were injected into the reactor simultaneously.
$^c$SBR standard trityl borate screening conditions.
$^d$Pre-mix catalyst and cocatalyst.
$^e$Zr(Bz)$_4$ as scavenger at 1.2 mmol/L.
$^f$Copolymerization with 20 mL of 1-octene. Polymerization activities were calculated based on polymer weight. 20.7 Br/1000 C detected by NMR for copolymer produced in run 9.
$^g$DuPont Ni diimine catalyst was synthesized according to a published procedure (L. K. Johnson, C. M. Killiam, M. Brookhart, J. Am. Chem. Soc., 117, 6414, 1995).

Part B: Gas Phase Polymerization
Catalyst Preparation and Polymerization Testing Using a Semi-Batch, Gas Phase Reactor The catalyst preparation methods described below employ typical techniques for the syntheses and handling of air-sensitive materials. Standard Schlenk and drybox techniques were used in the preparation of ligands, metal complexes, support substrates and supported catalyst systems. Solvents were purchased as anhydrous materials and further treated to remove oxygen and polar impurities by contact with a combination of activated alumina, molecular sieves and copper oxide on silica/alumina. Where appropriate, elemental compositions of the supported catalysts were measured by Neutron Activation analysis and a reported accuracy of ±1% (weight basis).

The supported catalysts were prepared by initially supporting MAO on a silica support, followed by deposition of the catalyst component.

All the polymerization experiments described below were conducted using a semi-batch, gas phase polymerization reactor of total internal volume of 2.2 L. Reaction gas mixtures, including ethylene were measured to the reactor on a continuous basis using a calibrated thermal mass flow meter, following passage through purification media as described above. A pre-determined mass of the catalyst sample was added to the reactor under the flow of the inlet gas with no pre-contact of the catalyst with any reagent, such as a catalyst activator. The catalyst was activated in situ (in the polymerization reactor) at the reaction temperature in the presence of the monomer, using a metal alkyl complex which has been previously added to the reactor to remove adventitious impurities. Purified and rigorously anhydrous sodium chloride was used as a catalyst dispersing agent.

The internal reactor temperature is monitored by a thermocouple in the polymerization medium and can be controlled at the required set point to +/−1.0° C. The duration of the polymerization experiment was one hour. Following the completion of the polymerization experiment, the polymer was separated from the sodium chloride and the yield determined. The following table illustrates bench scale gas phase reaction conditions.

Bench Scale Reactor Operating Conditions for Gas Phase Polymerizations

Examples 15 is an example of the gas phase polymerization. The next table illustrates data concerning the Al/transition metal ratios of the supported catalyst, polymer yield and polymer properties.

Polymerization Results
Part C: Slurry Phase Polymerization
Catalyst Preparation and Polymerization Testing Using a Semi-Batch, Gas Phase Reactor
Part C1: High Temperature and Pressure Slurry Polymerization The supported catalyst described in Part B was also used for the slurry polymerization tests.

All the polymerization experiments described below were conducted using a semi-batch reactor of total internal volume of 2.2 L. Reaction gas mixtures, including ethylene were measured to the reactor on a continuous basis using a calibrated thermal mass flow meter, following passage through purification media as described above. A pre-determined mass of the catalyst sample was added to the reactor under the flow of the inlet gas with no pre-contact of the catalyst with any reagent, such as a catalyst activator. The catalyst was activated in situ (in the polymerization reactor) at the reaction temperature in the presence of the monomer, using a metal alkyl complex and solvent which have been previously added to the reactor to remove adventitious impurities.

The internal reactor temperature is monitored by a thermocouple in the polymerization medium and can be controlled at the required set point to +/−1.0° C. The duration of the polymerization experiment was one hour. Following the completion of the polymerization experiment, the slurry was transferred from the reactor to a bowl, and the solvent was left to evaporate. The following table illustrates bench scale slurry phase reaction conditions.

Bench Scale Reactor Operating Conditions for Slurry Polymerizations

Examples 16 are high pressure and temperature slurry polymerization examples. The next table illustrates data concerning the Al/transition metal ratios of the supported catalyst; polymer yield and polymer properties.

Polymerization Results

Part C2: Low Temperature and Pressure Slurry Polymerization

Low pressure and temperature slurry polymerization experiments were conducted on a catalyst screening unit (CSU) where polymerization occurs in a cyclohexane reaction media, ethylene is fed to the reactor on demand and is monitored by a mass flow meter. On the CSU, reaction temperatures are monitored and controlled by thermocouples and one RTD. Reactor temperature control is maintained by a HAAKE circulating water bath which has external thermostatic control via the thermocouple at the reactor core. Reactor temperature is maintained by the water from the bath entering the jacket-like coolant chamber surrounding the reactor. Reaction pressures are indicated by mechanical pressure gauges and monitored manually.

The CSU shares the purified ethylene and cyclohexane feeds with the solution semi-batch reactor (SBR). Ultra-High-Purity argon from PRAXAIR which is purified further by 13x and OXICLEAR on a separate gas purification unit is used for reactor system purging and solvent sparging. The polymerization products are quantitatively recovered for mass determination, and polymerization activities are then calculated based upon mass of product, millimoles of catalyst injected and reaction time.

Examples 17–22 were conducted on a catalyst screening unit (CSU).

CSU Standard MAO Screening Conditions

CSU Standard Tritylborate Screening Conditions

CSU Polymerization Results

What is claimed is:

1. A complex of formula I:

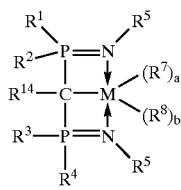

wherein M is a metal atom; $R^1$, $R^2$, $R^3$ and $R^4$ are independently selected from the group consisting of a saturated or unsaturated straight chained, branched or cyclic hydrocarbyl radical which is unsubstituted or substituted by one or more substituents selected from the group consisting of a halogen atom and a $C_{1-6}$ alkyl radical; $R^7$ and $R^8$ are independently selected from the group consisting of a halogen atom, an amide of the formula —$NR^1R^2$, imide of the formula=$NR^1$, alkoxide or aryl oxide group of the formula —$OR^1$, a siloxy group of the formula —$OSi(R^1)_3$ wherein $R^1$ and $R^2$ are defined above, and a saturated or unsaturated straight chained, branched or cyclic hydrocarbyl radical which is unsubstituted or substituted by a halogen atom or a $C_{1-6}$ alkyl radical and a Lewis base (neutral coordinating ligands); a and b are integers and a+b is an integer greater than 2 up to the sum of the valence and coordination number of M; and each $R^5$ is independently selected from the group consisting of radicals selected from the group consisting of saturated and unsaturated straight chained, branched and cyclic hydrocarbyl radicals, radicals of the formula $Si(R^6)_3$ wherein each $R^6$ is independently selected from the group consisting of saturated or unsaturated straight chained, branched or cyclic hydrocarbyl radicals, preferably $C_{1-10}$ saturated or unsaturated straight chained, branched or cyclic hydrocarbyl radicals and radicals of the formula III:

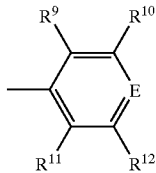

wherein $R^9$, $R^{10}$, $R^{11}$ and $R^{12}$ are independently selected from the group consisting of a hydrogen atom, a fluorine atom, a $NO_2$ radical, a $C_{1-6}$ alkyl radical and a $C_{8-12}$ aryl radical; and E is an endocyclic nitrogen atom or a C—CN group; and $R^{14}$ is selected from the group consisting of a hydrogen atom, a sulfur atom, an oxygen atom, an amido radical which is unsubstituted or may be substituted by $C_{1-20}$ alkyl radical or a radical of the formula —$Si(R^6)_3$ wherein $R^6$ is as defined above, a $C_{1-20}$ hydrocarbyl radical, a $C_{6-12}$ aromatic radical and a radical of the formula III as defined above, each of which may contain one or more functional groups including a heteroatom acting as a Lewis base; and optionally $R^{14}$ taken together with M may form a ring.

2. The complex according to claim 1, wherein M is selected from the group consisting of Y, Ti, Zr, Hf, V, Cr, Fe, Co, Ni, Pd, Zn and Sm.

3. The complex according to claim 2, wherein $R^1$, $R^2$, $R^3$ and $R^4$ are selected from the group consisting of $C_{1-10}$ straight chained, branched or cyclic alkyl radicals which are unsubstituted or substituted by up to three substituents selected from the group consisting of a chlorine atom, a fluorine atom and a $C_{1-4}$ alkyl radical and $C_{5-14}$ aromatic radicals which are unsubstituted or further substituted by up to n−1, wherein n is the number of carbon atoms in the aromatic radical substituents selected from the group consisting of a fluorine atom, a chlorine atom and a $C_{1-6}$ alkyl radical or an amido radical which is unsubstituted or substituted by up to two $C_{1-6}$ alkyl radicals.

4. The complex according to claim 3, wherein $R^7$ and $R^8$ are selected from the group consisting of a chlorine atom; a fluorine atom; an amide of the formula —$NR^1R^2$ wherein $R^1$ and $R^2$ are $C_{1-4}$ alkyl radicals; $C_{5-14}$ aromatic radicals which are unsubstituted or further substituted by up to n−1, wherein n is the number of carbon atoms in the aromatic radical substituents selected from the group consisting of a fluorine atom, a chlorine atom and a $C_{1-6}$ alkyl radical or an amido radical which is unsubstituted or substituted by up to two radicals independently selected from the group consisting of a methyl radical, an ethyl radical, a propyl radical, a butyl radical, a tertiary butyl radical and a phenyl radical; an imide of the formula=$NR^1$ wherein $R^1$ is as defined above; an alkoxide or aryloxide of the formula —$OR^1$ wherein $R^1$ is as defined above, a siloxy group of the formula —$O(R^1)_3$ wherein $R^1$ is as defined above; a $C_{1-10}$ straight chained, branched or cyclic alkyl radicals which are unsubstituted or substituted by up to three substituents selected from the group consisting of a chlorine atom, a fluorine atom and a $C_{1-4}$ alkyl radical; $C_{1-6}$ alkyl ethers, $C_{4-8}$ cyclic ethers; $C_{1-6}$ tertiary amines; cyclic $C_{4-8}$ nitrogen containing compounds; and tertiary $C_{1-10}$ phosphines.

5. The complex according to claim 4, wherein a+b is from 3 to 6.

6. The complex according to claim 5, wherein $R^{14}$ is selected from the group consisting of a hydrogen atom, an oxygen atom, an amido radical unsubstituted or may be substituted by $C_{1-6}$ alkyl radical or a radical of the formula —Si(R$^6$)$_3$ wherein R$^6$ is selected from the group consisting of methyl, ethyl, propyl and butyl radicals, a $C_{1-6}$ hydrocarbyl radical, a $C_{6-12}$ aromatic radical and a radical of the formula III:

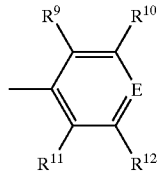

wherein $R^9$, $R^{10}$, $R^{11}$ and $R^{12}$ are independently selected from the group consisting of a hydrogen atom, a fluorine atom, a NO$_2$ radical, a $C_{1-6}$ alkyl radical and a $C_{8-12}$ aryl radical; and E is an endocyclic nitrogen atom or a C—CN group each of which hydrocarbyl radicals, aromatic radicals and radicals of formula III may contain one or more functional groups selected from the group consisting of:

(i) an amido group which may be unsubstituted or substituted by up to two substituents selected from the group consisting of $C_{1-6}$ alkyl radicals; a radical of the formula —Si(R$^6$)$_3$ wherein R$^6$ is as defined above; a phosphine group which may be unsubstituted or further substituted by a substituent selected from the group consisting of a hydrogen atom, a fluorine or chlorine atom, a $C_{1-6}$ alkyl or alkoxide radical, and an amide radical which is unsubstituted or substituted by up to two $C_{1-6}$ alkyl radicals;

(ii) an imido group which is unsubstituted or may be substituted by $C_{1-6}$ alkyl or $C_{6-12}$ aromatic radical; a radical of the formula —Si(R$^6$)$_3$ wherein R$^6$ is as defined above; an amido group as defined above; a phosphine group which may be unsubstituted or substituted by a substituent selected from the group consisting of a hydrogen atom, a fluorine or chlorine atom, a $C_{1-6}$ alkyl or alkoxide radical, and an amide radical which is unsubstituted or substituted by up to two $C_{1-6}$ alkyl radicals; and (iii) a phosphine group which may be unsubstituted or substituted by a substituent selected from the group consisting of a hydrogen atom, a fluorine or chlorine atom, a $C_{1-6}$ alkyl or alkoxide radical, and an amide radical which is unsubstituted or substituted by up to two $C_{1-6}$ alkyl radicals; and (iv) a carbonyl or carboxyl group.

7. The complex according to claim 6, wherein $R^1$, $R^2$, $R^3$ and $R^4$ are selected from the group consisting of a fluorine atom, a chlorine atom, a methyl radical, an ethyl radical, a propyl radical, a butyl radical, a tertiary butyl radical and a phenyl radical.

8. The complex according to claim 7, wherein one or more $R^5$ substituents are selected from the group consisting of $C_{1-6}$ alkyl radicals and $C_{6-12}$ cyclic aliphatic or aromatic radicals.

9. The complex according to claim 8, wherein $R^5$ is selected from the group consisting of methyl, ethyl, butyl, phenyl and adamantyl radicals.

10. The complex according to claim 7, wherein one or more $R^5$ substituents is a radical of the formula III:

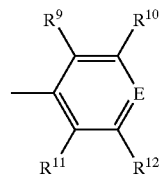

wherein $R^9$, $R^{10}$, $R^{11}$ and $R^{12}$ are independently selected from the group consisting of a hydrogen atom, a fluorine atom, a NO$_2$ radical, a $C_{1-6}$ alkyl radical and a $C_{8-12}$ aryl radical; and E is an endocyclic nitrogen atom or a C—CN group.

11. The complex according to claim 10, wherein E is an endocyclic nitrogen atom.

12. The complex according to claim 10, wherein E is a C—CN group.

13. The complex according to claim 7, herein one or more $R^5$ substituents is selected from the group consisting of radicals of the formula Si(R$^6$)$_3$ wherein each R$^6$ is independently selected from the group consisting of $C_{1-10}$ saturated or unsaturated straight chained, branched or cyclic hydrocarbyl radicals.

14. The complex according to claim 13, wherein R$^6$ is selected from the group consisting of methyl, ethyl, propyl and butyl radicals.

15. A process for preparing a complex of formula I:

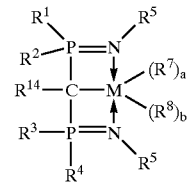

wherein M is a metal atom; $R^1$, $R^2$, $R^3$ and $R^4$ are independently selected from the group consisting of a saturated or unsaturated straight chained, branched or cyclic hydrocarbyl radical which is unsubstituted or substituted by one or more substituents selected from the group consisting of a halogen atom and a $C_{1-6}$ alkyl radical; $R^7$ and $R^8$ are independently selected from the group consisting of a halogen atom, an amide of the formula —NR$^1$R$^2$, an imide of the formula=NR$^1$, an alkoxide or aryl oxide group of the formula —OR$^1$, a siloxy group of the formula —OSi(R$^1$)$_3$ wherein R$^1$ and R$^2$ are defined above, and a saturated or unsaturated straight chained, branched or cyclic hydrocarbyl radical which is unsubstituted or substituted by a halogen atom or a $C_{1-6}$ alkyl radical and a Lewis base (neutral coordinating ligands); a and b are integers and a+b is an integer greater than 2 up to the sum of the valence and coordination number of M; and each $R^5$ is independently selected from the group consisting of radicals selected from the group consisting of saturated and unsaturated straight chained, branched and cyclic hydrocarbyl radicals, radicals of the formula Si(R$^6$)$_3$ wherein each R$^6$ is independently selected from the group consisting of saturated or unsaturated straight chained, branched or cyclic hydrocarbyl radicals and radicals of the formula III:

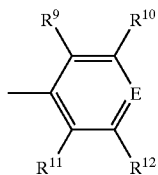

wherein $R^9$, $R^{10}$, $R^{11}$ and $R^{12}$ are independently selected from the group consisting of a hydrogen atom, a fluorine atom, a $NO_2$ radical, a $C_{1-6}$ alkyl radical and a $C_{8-12}$ aryl radical; E is an endocyclic nitrogen atom or a C—CN group; and $R^{14}$ is selected from the group consisting of a hydrogen atom, a sulfur atom, an oxygen atom, an amido radical which is unsubstituted or may be substituted by $C_{1-20}$ alkyl radical or a radical of the formula —$Si(R^6)_3$ wherein $R^6$ is as defined above, a $C_{1-20}$ hydrocarbyl radical, a $C_{6-12}$ aromatic radical and a radical of the formula III as defined above, each of which may contain one or more functional groups including a heteroatom acting as a Lewis base; and optionally $R^{14}$ taken together with M may form a ring comprising reacting a complex of formula II:

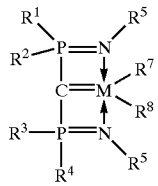

wherein $R^1$, $R^2$, $R^3$, $R^4$, $R^5$, $R^7$, $R^8$, a, b and M are as defined above with:

(i) molecules of the type AB where in A is selected from the group consisting of a hydrogen atom, a $C_{1-20}$ alkyl group, a $C_{6-12}$ aryl group, an amido radical which is unsubstituted or may be substituted by $C_{1-20}$ alkyl radical or a radical of the formula —$Si(R^6)_3$ wherein $R^6$ is as defined above, an $C_{1-20}$ alkoxy group, a $C_{1-20}$ alkylthio group, a $C_{6-12}$ aryloxy group, a $C_{6-12}$ arylthio group, and a radical of the formula III as defined above; and B is selected from the group consisting of a hydrogen atom provided that A is not a hydrocarbyl radical or a hydrogen atom, and halogen atom;

(ii) compounds of the formula F=C=G wherein F and G are independently selected from the group consisting of an O or S atom, and radicals of the formula=N—$R^{15}$, wherein $R^{15}$ is a $C_{1-20}$ hydrocarbyl radical, a $C_{6-12}$ aromatic radical, and a radical of the formula —$Si(R^6)_3$ wherein $R^6$ is as defined above; =P—$(R^{16})_d$ wherein d is 1 or 3; and $R^{16}$ is selected from the group consisting of a hydrogen atom, a halogen atom, $C_{1-20}$ hydrocarbyl radical, a $C_{1-20}$ alkoxide radical, a $C_{6-12}$ aromatic radical, a $C_{6-12}$ aryloxide radical, and radicals of the formula —$Si(R^6)_3$ or —O—$Si(R^6)_3$ wherein $R^6$ is as defined above.

* * * * *